(12) United States Patent
Warburton

(10) Patent No.: US 6,632,674 B1
(45) Date of Patent: Oct. 14, 2003

(54) METHOD OF TESTING GAS DETECTION INSTRUMENTS AND ASSOCIATED APPARATUS

(75) Inventor: P. Richard Warburton, Moon Township, PA (US)

(73) Assignee: Industrial Scientific Corporation, Oakdale, PA (US)

(*) Notice: Subject to any disclaimer, the term of this patent is extended or adjusted under 35 U.S.C. 154(b) by 0 days.

(21) Appl. No.: 09/282,661

(22) Filed: Mar. 31, 1999

(51) Int. Cl.⁷ .......................... G01N 37/00; G01N 33/00

(52) U.S. Cl. .................... 436/8; 436/9; 436/181; 73/1.02; 73/1.06

(58) Field of Search ..................... 436/8, 9, 181; 73/1.02, 1.06

(56) References Cited

U.S. PATENT DOCUMENTS

| | | |
|---|---|---|
| 3,247,702 A * | 4/1966 | Houser et al. ............... 436/39 |
| 3,960,495 A | 6/1976 | Tantram |
| 3,983,086 A | 9/1976 | Dickens, Jr. |
| 4,116,612 A | 9/1978 | Melgaard |
| 4,151,738 A | 5/1979 | Hyer et al. |
| 4,252,932 A | 2/1981 | Homan et al. |
| 4,267,030 A * | 5/1981 | Breuer et al. ............... 204/278 |
| 4,271,289 A | 6/1981 | Homan et al. |
| 4,384,925 A | 5/1983 | Stetter et al. |
| 4,394,239 A * | 7/1983 | Kitzelmann et al. ........ 204/414 |
| 4,399,942 A | 8/1983 | Chand |
| 4,532,229 A | 7/1985 | Fiato et al. |
| 4,624,967 A | 11/1986 | Fiato et al. |
| 4,642,172 A | 2/1987 | Fruhwald |
| 4,776,203 A | 10/1988 | Jones et al. |
| 5,198,771 A | 3/1993 | Fidler et al. |
| 5,202,637 A | 4/1993 | Jones |
| 5,239,492 A | 8/1993 | Hartwig et al. |
| 5,283,697 A | 2/1994 | Tutt et al. |
| 5,354,784 A | 10/1994 | Timmons et al. |
| 5,395,501 A | 3/1995 | Rohrbacker et al. |
| 5,558,752 A | 9/1996 | Wang et al. |
| 5,611,909 A | 3/1997 | Studer |
| 5,616,823 A | 4/1997 | Lattimore |
| 5,668,302 A * | 9/1997 | Finbow et al. ............... 73/23.2 |
| 5,959,188 A * | 9/1999 | Deutsch et al. .............. 73/1.06 |
| 6,098,523 A * | 8/2000 | Warburton ................... 73/1.06 |

FOREIGN PATENT DOCUMENTS

| | | |
|---|---|---|
| EP | 0 890 837 A2 | 1/1999 |
| WO | WO 93/05122 | 3/1993 |
| WO | WO 98/25139 | 6/1998 |

OTHER PUBLICATIONS

Chang et al., *Amperometric Gas Sensors*, Review, 1993, pp. 461–477, vol. 40, No. 4, Pergammon Press Ltd., Great Britain.

Bennett, *The Chemical Formulary—Collection of Commercial Formulas for Making Thousands of Products in Many Fields*, vol. XXXIV, 1997, pp. 106–113, Chemical Publishing Co., Inc., New York, US.

Mitchell, *Smoke Reduction from Burning Crude Oil Using Ferrocene and Its Derivatives*, Combustion and Flame, 1991, pp. 179–184, vol. 86, The Combustion Institute, Elsevier Science Publishing Co., Inc.

Davis et al., *The Addition of Halogenocarbons to Alkenes in the Presence of $[Fe_2(CO)_4(\eta-C_5H_5)_2]$ and Related Complexes*, Journal of Organometallic Chemistry, 1990, pp. 229–239, vol. 386, Elsevier Sequoia S.A., The Netherlands.

Hu et al., *Crystal Structures of Bis(Cyclopentadienyldicarbonyliron) Sodium Tetrahydrofuran and (Cyclopentadienyldicarbonyliron) Sodium Tetramethylethylenediamine Complexes*, Journal of Organometallic Chemistry, 1989, pp. 137–143, vol. 377, Elsevier Sequoia S.A., The Netherlands.

Zhang and Brown, *Studies of Intermediates in Photoreactions of $Cp_2Fe_2(CO)_4$ with CO and Phosphorus Ligands*, J. Am. Chem. Soc., 1993, pp. 1779–1789, vol. 115, US.

Farrugia and Mustoo, *Fluxionality of $Fe_2(CO)_4(\eta-C_5H_5)_2$ Revisited*, Organometallics, 1992, pp. 2941–2944, vol. 11, U.K.

McCutcheon's, *vol. 2: Functional Materials*, North American Edition, 1992, pp. 262–264, McCutcheon Division, MC Publishing Co., Glen Rock, NJ, US.

Harrison and Richmond, *Reductive Defluorination of Saturated Perfluorocarbons by Organometallic Nucleophiles*, J. Am. Chem. Soc., 1993, pp. 5303–5304, vol. 115, U.S.

Cotton and Wilkinson, *Advanced Inorganic Chemistry*, Fifth Edition, 1988, pp. 1021–1328, Chapter 22, U.S.

Latimer and Hildebrand, *Reference Book of Inorganic Chemistry*, 1940, pp. 240–242, Chapter XII, The Macmillan Company, NY, US.

Primary Examiner—Jill Warden
Assistant Examiner—LaToya Cross
(74) Attorney, Agent, or Firm—Arnold B. Silverman; David C. Jenkins; Eckert Seamans Cherin & Mellott, LLC

(57) ABSTRACT

A method for testing gas detection instruments includes providing at least two reagents, immobilizing at least one of the reagents into a matrix material, heating the matrix material until the matrix permits movement of the reagent and generating a gas responsive to chemical reaction between the reagents. The gas is introduced into the sensor portion of the gas detection instrument to test the same. The reagents may each be immobilized on the matrix material with the heating serving to soften or melt the matrix material to permit chemical interaction. In a preferred embodiment, the heating is effected at about 90 to 150° C. The method may be employed to generate carbon monoxide or other gases of interest. Corresponding apparatus is provided. The apparatus may be structured to be inserted into or receive the gas detection instrument or have its output in communication therewith.

21 Claims, 5 Drawing Sheets

OTHER PUBLICATIONS

*The Merck Index an Encyclopedia of Chemicals, Drugs, and Biologicals*, 1996, pp. 823 and 349, Twelfth Edition, Merck & Co., Inc., NJ, US.

Nelson, *Gas Mixtures Preparation and Control*, 1992, Lewis Publishers, Inc., US.

Horowitz and Hill, *The Art of Electronics*, 1980, Cambridge University Press, US.

U.S. Department of Health and Human Services, *Pocket Guide to Hazards*, NIOSH, pp. 54, 58 and 288.

*A World of Gases . . . A Single Transmitter—ATI Presents A Simpler Approach to Toxic Gas Detection*, (8 pgs.), Unisens, US.

Moseley et al., *Techniques and Mechanisms in Gas Sensing—Liquid Electrolyte Fuel Cells*, 1991, pp. 161–188, Chapter 6.

Firth, *Detection and Measurement of Hazardous Gases—Measurement of Flammable Gases and Vapours*, pp. 29–67, Chapter 2, Heinemann Educational Books Ltd., Great Britain.

\* cited by examiner

METHOD OF TESTING GAS DETECTION INSTRUMENTS AND ASSOCIATED APPARATUS

BACKGROUND OF THE INVENTION

1. Field of the Invention

This invention provides a method and related apparatus for checking the reliability of gas detection instruments through the generation of a test gas and its application to the gas detection instrument.

2. Description of the Prior Art

The reliability of toxic gas detectors is of great importance in many applications, especially when these instruments are used for ensuring the safety of personnel. Reliability is typically obtained by periodic checking of the instrument response to a test gas, however calibration test gases are typically supplied in large, bulky and expensive gas cylinders.

Potentially hazardous atmospheres are found in many locations, due to the presence of toxic gases, combustible gas mixtures or the excess or deficiency of oxygen concentration. Many types of gas detection instruments have been developed to provide a warning that the atmosphere contains potentially hazardous components, or to initiate remedial action. Examples of these gas detection instruments include the detection of combustible gases (primarily methane) in coal mines, hydrogen sulfide in oil fields and water treatment plants, carbon monoxide in places ranging from steel mills to bedrooms, and oxygen in confined spaces, such as sewers. Within each gas detection instrument there are one or more gas sensors, whose function is to provide an electrical signal, which varies in response to the gas concentration.

Many types of sensor technology are used for gas detection, including electrochemical, infrared, catalytic bead (heat of combustion), and tin oxide sensors. Details of these various sensor types are discussed in standard texts such as C. F. Cullis, J. G. Firth, "Detection and Measurement of Hazardous Gases", Heinemann, London, 1981; P. T. Mosely, J. O. W. Norris, D. E. Williams (Eds.), "Techniques and Mechanisms in Gas Sensing", Adam Hilger, Bristol, 1991. Each of these various technologies have different advantages and weaknesses, such that the method used will depend on the gas to be detected and the application requirements.

In general, most gas sensors provide a relative output signal, such that the output signal is not an absolute measure of the gas concentration. Instead the response is typically proportional to the gas concentration, with an empirically determined proportionality constant. Before the instrument can be used to measure the concentration of a gas, the instrument is first exposed to a known test gas concentration and the output signal correlated with the known gas concentration. This process is known as calibration.

Another role of calibration is to provide a function check to confirm that the gas detection instrument is operating correctly. Unfortunately, the output from many types of sensors can vary over time and in some cases sensors can fail to operate correctly without warning. It is therefore desirable to re-calibrate the sensor periodically. The interval between calibrations will depend on the sensor technology and on the accuracy requirements of the application. For example, electrochemical gas sensors, which are widely used for toxic and oxygen gas detection in industrial work place safety applications, are typically re-calibrated monthly; while many infrared combustible gas sensors may only require calibration every six months or every year.

Calibration is often a time consuming process, but for critical applications such as safety monitoring, a more frequent calibration interval may be used than is employed for a less critical application. One method commonly employed to reduce the burden of calibration is to perform a so-called "bump test", in which the instrument is exposed to a test gas of sufficiently high concentration to activate the warning alarms for a short period of time. If the instrument alarms are actuated, then the instrument is deemed to be working correctly. However, if the instrument alarms do not actuate, then the instrument requires servicing. While calibration of the instrument is usually performed with test gases with concentrations known to a high degree of accuracy, bump tests are often performed with a more economical test gas mixture whose concentrations are known to a lower degree of accuracy.

Test gases are commonly available in compressed gas cylinders. For everyday use, small hand-held, disposable gas cylinders are widely used. Unfortunately, the use of disposable gas cylinders is both expensive and cumbersome, due to the requirements of safely containing and using compressed gases.

Alternative methods of test gas generation have been developed. Electrochemical gas generators, such as those disclosed in U.S. Pat. No. 5,395,501, are available for several gases including hydrogen sulfide, chlorine, and chlorine dioxide. Electrochemical gas generators are obviously limited to those gases that can be produced by an electrochemical reaction. As for any electrochemical reaction, the amount of product produced is linearly proportional to the current passing, as described by Faraday's law, and the diluent gas flow can be readily controlled, electrochemical generators in principle can provide good control over the gas concentration. In practice, the effects of absorption, changes in electrolyte composition, competitive electrode reactions and errors in the gas flow control limit the accuracy of these devices.

Calibration methods have also been devised in which the test gas is periodically generated, under the control of a microprocessor or other controller within the gas detection instrument. This approach allows the instrument to perform a gas test on the instrument without the need for a human operator. For example, electrochemical gas generators are used by Analytical Technology Inc. of Oaks, Pa. 19456 (8 Page Technical Information Sheet, entitled *A world of gases . . . A single transmitter*) to provide test gas to automatically check the performance of gas detection instruments, and ensure that the sensors are responding within their specified limits.

Automatic calibration methods have also been described in the prior art. For example, U.S. Pat. Nos. 4,384,925, 4,151,738, 5,239,492 and 4,116,612 describe methods for automatic calibration of a gas detection instrument in which calibration gas is automatically applied to the sensors under the control of a microprocessor. However, in most of these examples, the source of the test gas is still a compressed gas cylinder.

Electrochemical gas generators have also been incorporated into gas detection instruments. See, for example U.S. Pat. No. 5,668,302 and PCT International application WO 98 25139 which describe the incorporation of an electrochemical gas generator into an electrochemical gas sensor. These electrochemical gas generators have been used for carbon monoxide sensors, though the test gas produced is hydrogen from the electrolysis of the aqueous sulfuric acid electrolyte. In this latter example, while the incorporation of the gas generator into the sensor has clear advantages, it would be desirable to test the sensor with the intended analyte gas, in this case carbon monoxide, instead of the surrogate gas, hydrogen. The electrochemical properties of hydrogen are very different from carbon monoxide, and the oxidation of the latter gas is highly dependent upon the catalytic nature of the electrode surface. As a result, a good response of the sensor to hydrogen does not guarantee that the sensor will perform equally well to carbon monoxide.

Permeation-tubes are another commonly used device for producing calibration gases. These devices typically contain a polymeric tube containing the liquefied gas in an air stream. As the internal gas concentration is constant and the external concentration is near zero, the diffusion rate of gas through the polymeric material will be constant for a constant temperature. While permeation tubes are widely used to provide laboratory test gases, their use in field calibrators is limited due to the requirement for very tight control (e.g. +/-0.1° C.) of the temperature for accurate gas generation. Despite the difficulties, portable instruments are commercially available, e.g. from Kin-Tech, Houston Tex. Also, the use of permeation ovens is generally limited to gases that are readily available in liquid form at ambient temperature.

The use of permeation ovens for permanent gases is possible, by frequently refilling the reservoir container, but this requirement restricts the applicability of this method and adds to both the experimental complexity and expense.

Chand recently described a modification to the permeation tube method to produce test gas concentrations with less dependence on the absolute temperature than conventional permeation devices. See U.S. Pat. No. 4,399,942. Various injection methods are used for producing gas mixtures in laboratory scale, but these methods are not often used for field calibration. See Gas Mixture, Preparation and Control, G. O. Nelson, Lewis Publ., Boca Raton, Fla. (1992).

In another approach, U.S. Pat. No. 3,960,495 described a test gas system for combustible gas sensors, whereby a small amount of combustible gas is constantly generated by evaporation of a combustible material in the vicinity of the sensor. A decrease in the constant background signal indicates failure of the sensor. However, as the vapor pressure of most organic liquids depends very strongly on temperature, the concentration of test gas generated will fluctuate with temperature and as a result, the output signal will also fluctuate with temperature.

Alternatives to using test gas have also been investigated. For infrared-based gas sensors, various approaches have been tried including the use of optical filters. See U.S. Pat. No. 5,616,823, wherein the change in light intensity reaching the detector on inserting a filter of known absorbance into the light path, is used to calibrate the instrument. Methods have also been developed to assess the status of electrochemical gas sensors based on applying or perturbing the bias potential. Examples of this approach have been described for exhaust gas oxygen sensors in U.S. Pat. No. 5,558,752 and for toxic gas sensors in U.S. Pat. Nos. 5,202,637 and 5,611,909.

All of these alternative methods test only one aspect of the function of the gas sensor, and if the sensor is failing in this aspect then the test will identify the problem. However, these tests typically fail to test all aspects of the gas detection process. For example, an optical filter will test the change in absorbance of infrared light reaching the detector, but it will be unable to test whether the gas path into the sensor is accessible. Similarly, electrical perturbations to an electrochemical sensor test the integrity of the electrode connections, but would fail to detect a blocked membrane or other component in the gas diffusion path. Clearly, these substitute tests have value, but they fail to provide the reliability that the sensor is operating correctly, obtained by testing the gas sensor with the intended analyte gas.

A gas generator has been disclosed by the present inventor in European application EP 890 837 A2 for checking a carbon monoxide gas sensor. The gas generator disclosed therein includes a resistor or resistor array with a coating containing an oxalate salt. By applying an electrical potential to one of the resistors, a rise in temperature occurs until carbon monoxide is produced as a result of thermal decomposition of the oxalate salt. The system requires temperatures in the range of about 150 to 300° C. thereby necessitating a large power supply and effective thermal insulation from the rest of the gas detection instrument. Also, it discloses solely the production of carbon monoxide.

There are many so-called "wet chemical" methods available for the laboratory scale production of gases, which are well known (The Merck Index, $12^{th}$ Edition, (1996); W. M. Latimer, J. H. Hilderbrand, "Reference Book of Inorganic Chemistry, MacMillan Co., New York, 1940). Using these methods a wide variety of gases can be prepared. The difficulty in using these types of reaction for test gas generation is to prevent the mixing of the reagents prior to use, and control the mixing of the reagents when test gas is required.

In spite of the foregoing prior art teachings, there remains a need for a single system that can produce several different types of gas. The use of multiple gas generation technologies adds both expense and complexity to the gas delivery system and probably also the gas detection equipment. As many gas detection instruments measure more than one type of gas, or similar instruments are available for different gas types by minor modification of the either the sensor or the instrument, a common gas-generating technology is advantageous. This system should be able to produce a concentration of test gas suitable for providing either a calibration or a bump test for a gas detection instrument. The equipment should be small, economical, simple and easy to use.

SUMMARY OF THE INVENTION

The above described need has been met by the present invention.

A method of generating test gases at the point of use, involving mixing of two or more chemical reagents together, which when combined result in the emission of the test gas. These reagents are mixed with a solid matrix material. The matrix material is selected such that the reagents are unable to react together at ambient temperature. Upon heating the mixture to a sufficiently high temperature that the matrix material melts, one of more of the reagents dissolves in the matrix, thus allowing the reagents to mix and produce the test gas. Related apparatus is disclosed. This system can be included within a gas detection instrument, or in a separate device intended to supply test gas to a gas detection instrument.

By holding the reagents in a solid matrix, the reagents will only mix if the temperature were raised above the melting point of the matrix. By placing this mixture of the matrix material together with the reagents in contact with a heating element, then the generation of the test gas can be controlled by controlling the electrical power to the heating element. Preferably, the two reagents should be solid, or high viscosity liquids for ease of handling. At least one of the reagents should be soluble in the matrix material, such that it will dissolve into the matrix, when the matrix is heated to above its melting point. Dissolution of the reagent will allow it to travel by diffusion processes to the other reagent(s) whereupon they will react and produce the test gas.

If the gas-generating element, comprised of the matrix material, reagents and suitably juxtapositioned heating element, is placed near the gas entry path of a gas detection instrument, then upon activation of the heater, test gas will be produced, which will then enter the gas detection instrument. Suitable positioning of the gas-generating element may involve inclusion within the gas detection instrument, inclusion within a calibration cup (a commonly used device which fits over part of the gas detection instrument, to deliver gas to the instrument during calibration), or as part of sample pump adapter. Alternatively the gas-generating element may be in a separate unit, and delivered to the gas detection instrument by conventional means, such as by flexible tubing. The test gas generated may enter the gas detection instrument by diffusion, or it may be blended with diluent gas, such as clean air or nitrogen, and then applied to the sensor. Alternatively, for instruments equipped with sample draw pumps, the test gas may be drawn into the instrument, preferably combined with ambient or filtered air. By varying the reagents and the matrix material gas-generating elements can be produced for many different types of test gas.

A preferred method of the present invention for testing gas detection instruments includes providing two reagents that would react with each other chemically to produce the test gas, except that mixing of the two together adequately is resisted, either because they are both in solid form and held by the matrix, or because they are a liquid and are immobilized in a matrix material. For convenience of reference herein, either of these situations, as well as other conditions under which one or more matrix materials serve to resist mixing of two or more reagents so as to resist premature meaningful chemical reactions which create test gases will be referred to as "immobilizing" the reagent. The matrix material is subsequently heated until the matrix permits movement of one or more of the reagents resulting in generation of a gas responsive to a chemical reaction between the reagents and employing the gas to test the gas detection instrument. If desired, more than two reagents may be employed and more than a single test gas may be generated.

The matrix is preferably heated to facilitate dissolution or mobilization, or both, of one or more reagents. A second reagent may be immobilized in a second portion of the matrix material and if desired, an interposed portion of the matrix material may be provided to establish a physical barrier between the two reagent containing matrix portions. Corresponding apparatus is provided.

It is an object of the present invention to provide a test gas-generating system which resists chemical reagent interaction until it is desired to generate the test gas.

It is a further object of the present invention to provide such a system wherein at least one of the reagents is immobilized in a matrix material and is subjected to heating when it is desired to permit chemical interaction between reagents to generate one or more test gases.

It is a further object of the present invention to provide such a system which may generate the gas within the gas detection instrument or externally thereof.

It is yet another object of the present invention to provide efficient means for testing the effectiveness of a gas detection instrument with respect to one or more gases being monitored by the gas detection instrument.

It is yet another object of the present invention to provide such a system wherein microprocessors may be employed to control the operation of the test gas generation.

It is yet another object of the present invention to provide such a system which may employ reagents which are liquid or solid.

It is yet another object of the invention to provide a self-contained, thermally activatable test gas generator which is capable of generating one or more test gases.

It is yet another object of the present invention to provide such a test gas-generating system which may be utilized externally of or within a gas detection instrument or may receive the gas detection instrument within the test gas-generating system.

These and other objects of the invention will be fully understood from the following description of the invention with reference to the drawings appended hereto.

DESCRIPTION OF THE PREFERRED EMBODIMENTS

As used herein, the term "reagent" means a material which when chemically interacted with one or more other reagents will produce a desired test gas or gases.

The gas-generating method and related apparatus of the present invention can be used to determine the functional state of, for example, portable instruments, hand held instruments, or instruments which are fixed in a particular location, such as, for example, wall mounted instruments. The gas-generating apparatus comprises a matrix material which is solid at ambient temperature, but which melts or softens at higher temperature. Two or more solid, high viscosity or otherwise immobilized reagents, such as a liquid absorbed onto porous support, are incorporated into the matrix material. The reagents are selected such that they will react together chemically to produce a test gas upon mixing with each other. The matrix and the reagents are selected such that at least one of the reagents is soluble in the matrix material once it has softened or melted. By varying the matrix material and the reagents, different test gases may be generated.

If all of the reagents are solid, such that there is no reaction between the reagents at ambient temperature within the matrix material, then the matrix material can have reagents intimately mixed therein. For those reagents, which will slowly react together, even when the matrix material is solid, then the matrix may be deposited in two or more separate layers, each layer containing one or more of the reagents. When the matrix is heated, the matrix material will melt or soften and the reagents from the layers will mix, react chemically and produce the test gas. If there is still an unacceptably high level of reaction, the matrix can be deposited in three layers, with one of the two reagents in the bottom layer, the other reagent in the top layer and only matrix material in the middle layer. The middle layer will act as a buffer between the top and bottom layers.

Figure 1:
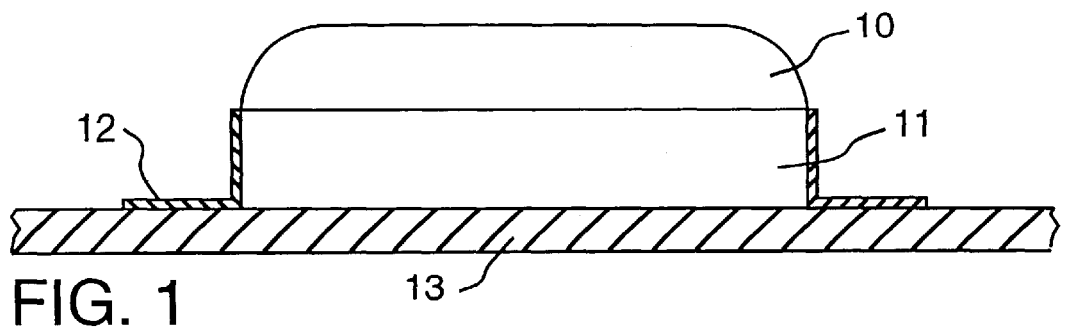
FIG. 1 is a partially schematic cross-sectional illustration of a form of test gas-generating apparatus of the present invention.
Figure 2:
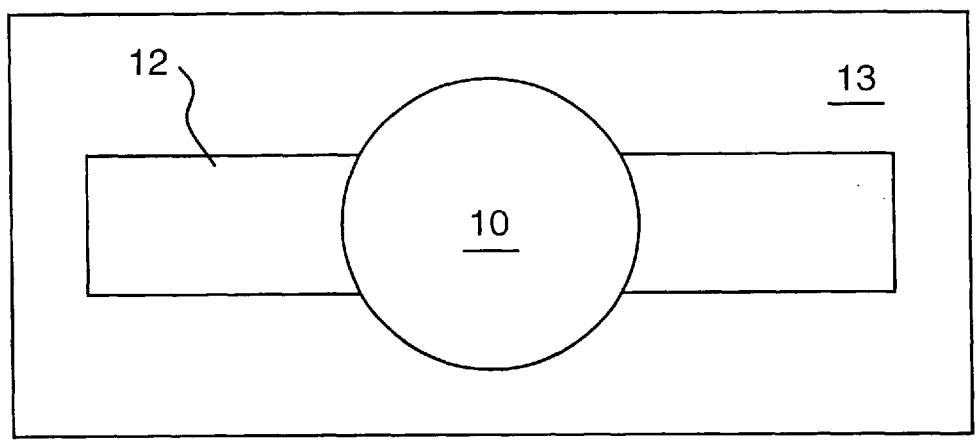
FIG. 2 is a top plan view of the test gas-generating apparatus of FIG. 1.

Typically the mixture of the matrix material and reagent or reagents will be placed in thermal contact with a heater as shown in FIGS. 1 and 2. In order for test gas to be produced, the matrix material 10 in combination with the reagent or reagents are heated. This heating may be done by any of the conventional ways known in the prior art. In one embodiment of this invention, the matrix material 10 in combination with the reagents is deposited onto the surface of an electrical resistance heater 11, or onto a thermal conductor which is in contact with an electrical resistance heater. The electrical resistive heater 11 is placed on a suitable support 13, such as a circuit board, for example, which also provides the electrical contacts 12 for energizing the heater 11. The electrical resistance heaters 11 may, for example, include surface mount resistors on a printed circuit board, or metallic tracks in a polymeric substrate, such as those commercially available from Minco Products Inc. of Minneapolis, Minn.

Figure 3:
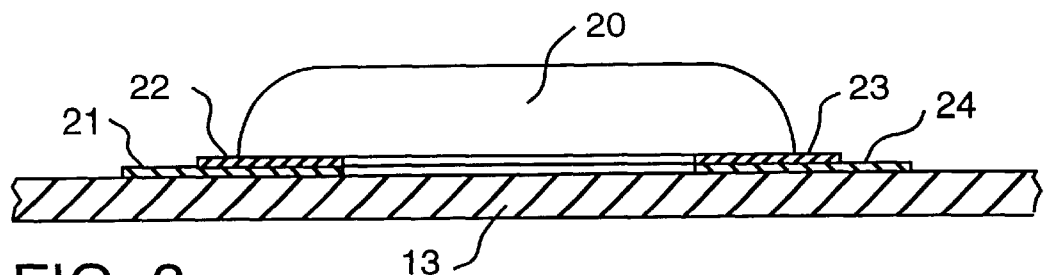
FIG. 3 is a partially schematic cross-sectional illustration of another embodiment of test gas-generating apparatus of the present invention.

In another embodiment of this invention, shown in FIG. 3, a metallic conductor, such as gold or graphite powder, may be mixed into the matrix material and reagent mixture, in sufficient quantity to produce an electrically conductive material 20. This electrically conductive matrix material 20, is placed between two electrical contacts 22, 23 on a support 13. Electrical power may be supplied to the electrical contacts 22, 23 by conventional electric conductors 21, 24. Applying an electrical potential between the said electrical contacts 22, 23 heats the matrix 20 and generates the test gas.

Figure 4:
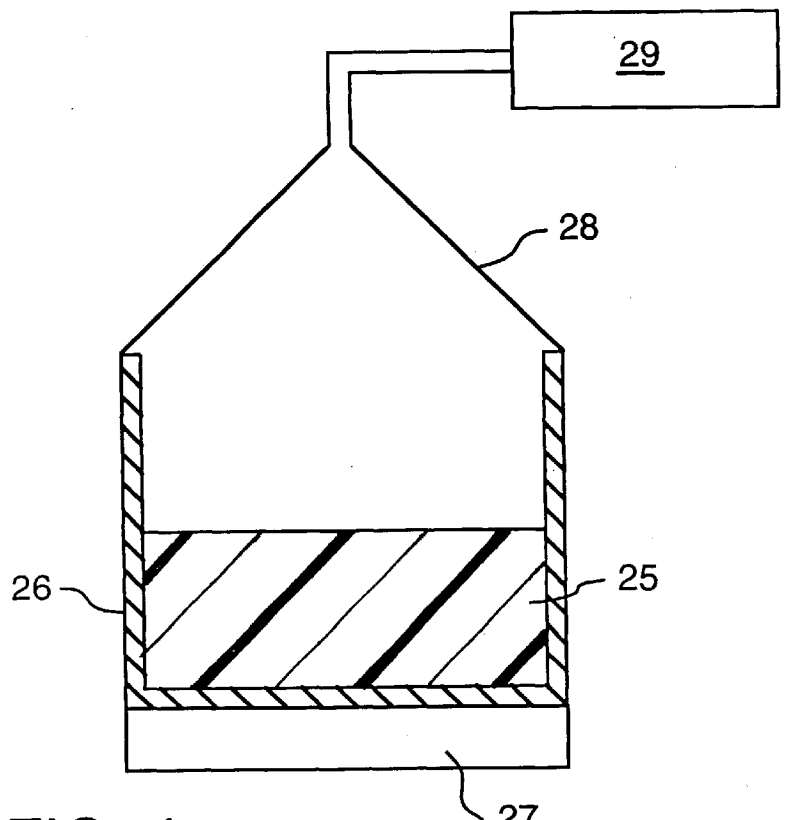
FIG. 4 is a cross-sectional illustration of another form of test gas-generating apparatus of the present invention.

Alternative configurations may also be employed within the scope of this invention. For example, as shown in FIG. 4, the mixture of the matrix material 25 and the two or more reagents can be placed within a metallic can 26, with the can being in thermal contact with an electrically energized heating element 27. Upon activation of the heating element 27, the heat produced will be transferred to the can 26, and its contents. Upon being heated to a temperature greater than the melting point of the matrix material 25, one or more of the reagents will dissolve in the molten matrix material 25, allowing the reagents to react to produce the test gas which enters conduit 28 for delivery to the gas detection instrument 29.

Using the production of carbon monoxide gas as an example; a suitable reaction, which will produce carbon monoxide involves reaction of a transition metal carbonyl-containing complex. Many transition metal carbonyl and carbonyl containing compounds are known (F. A. Cotton, G. Wilkinson, "Advanced Inorganic Chemistry", $5^{th}$ Edition, John Wiley and Sons, New York, 1988). In most cases the carbon monoxide is easily removed from transition metal carbonyl complexes by the action of heat, oxidizing agents or light, for example. Most carbonyl complexes, however, present practical problems of low vapor pressure, instability, high reactivity or other potential hazards. For example, nickel carbonyl [$Ni(CO)_4$], is a very toxic and volatile liquid (melting point (MP) $-25°$ C.), and iron carbonyl [$Fe(CO)_5$] is a yellow liquid (MP $-20.5°$ C.) which decomposes on contact with air. While most of the carbonyl containing complexes lack the necessary chemical stability and physical form for use as a reagent in the system of the present invention, a few stable substituted carbonyl complexes do exist, which have the requisite properties. The preferred transition metal carbonyl complexes are solid at ambient temperature ($<60°$ C.), and which are stable in air to temperatures greater than $100°$ C. An example of a preferred transition metal carbonyl complexes is manganese pentacarbonyl bromide [$Mn(CO)_5Br$]; and the most preferred complex is bis(iron cyclopentadienyl dicarbonyl), [$Fe(C_5H_5)(CO)_2$]$_2$.

Bis(iron cyclopentadienyl dicarbonyl) is known in the chemical literature. It has been studied as a model compound for carbon monoxide scrambling (F. A. Cotton, G. Wilkinson, "Advanced Inorganic Chemistry", $5^{th}$ Edition, John Wiley and Sons, New York, 1988; L. J. Farrugia, L. Mustoo, *Organometallics*, (1992), 11, 2941) and for its reactions with other ligands (S. Zhang, T. L. Brown, *Journal of the American Chemical Society* (1993), 115, 1779; N. Hu, G. Nie, Z. Jin, W. Chen, *Journal of Organometallic Chemistry*, (1989), 377, 137). This compound has also been studied as a catalyst for the addition of halogen carbons to alkenes (R. Davis, J. L. A. Durrant, N. M. S. Khazal, T. E. Bitterwolf; *Journal of Organometallic Chemistry*, (1990), 386, 229) and as a catalyst for the polymerization of mercapto-organosilane resins (U.S. Pat. Nos. 4,252,932 and 4,271,289); and its use in the polymerization of cyanate ester adhesives has been disclosed in International Patent Application (PCT) WO 93/05122. It has been described using this compound, bis(iron cyclopentadienyl biscarbonyl), as a precursor for a Fischer Tropsch catalyst for alpha olefin production in U.S. Pat. Nos. 4,532,229 and 4,624,967.

Some other uses of bis(iron cyclopentadienyl biscarbonyl) include use as a soot reducing agent for burning crude oil (J. B. A. Mitchell, *Combustion and Flame* (1991), 86, 179), and analogously as an additive for vinyl chloride for retarding smoke formation. See U.S. Pat. No. 3,983,086. It has also been investigated as a reagent for defluorinating perfluorocarbons (R. G. Harrison, T. G. Richmond, *Journal of the American Chemical Society* (193), 115, 5305), and as a precursor of a photoabsorbent material to provide passive protection against intense light sources, as disclosed in U.S. Pat. Nos. 5,283.697 and 5,354,784.

It has been found that the bis(iron cyclopentadienyl biscarbonyl) complex can be oxidized by strong oxidizing agents to produce carbon monoxide. A preferred oxidizing agent is manganese dioxide ($MnO_2$). There are many other strong oxidizing agents known in art which may also be used, including permanganate, chlorate, iodate, bromate, chromate salts with alkali metal and alkaline earth metal ions; metal oxides, such as manganese dioxide, chromium (VI) oxide, and high valent metal ions, such as cerium (IV) and organic oxidizing agents, such as benzoyl peroxide [$C_6H_5CO)_2O_2$] (Benzoyl peroxide, however, can explode on heating).

In heating to generate test gases, the preferred temperature range is preferably greater than the normal upper operating temperature of most gas detection instruments, +50° C. is typical, but not so high as to require excessive power or thermal insulation. The temperature range will typically be in the range of about 60° C. to 400° C., and preferably in the range of about 80 to 200° C. The most preferred range is from about 90 to 150° C.

The matrix material should be chosen, such that one or more of the reagents is soluble in the matrix, with the matrix being chemically compatible with all of the other ingredients. The melting point of the matrix material should be in the desired temperature range. Using carbon monoxide test gas generation as an example, the metal carbonyl, $[Fe(C_5H_5)(CO)_2]_2$, is soluble in many low to moderate polarity nonaqueous solvents, such as toluene and tetrahydrofuran. As in this example, manganese dioxide is not soluble in most liquids, the matrix material is selected such that the bis(iron cyclopentadienyl biscarbonyl) complex will dissolve in the matrix when the matrix is heated to a molten state. Therefore, the matrix material should be a compound of low polarity, with a melting point at a convenient temperature.

Preferred matrix materials for carbon monoxide generation include molecular compounds, such as 1,10phenantroline, phenanthrene, or polymeric materials such as polybutylene, polyethylene co-carbon monoxide. The most preferred matrix material for carbon monoxide generation is low-density polyethylene. There are many matrix materials in which one of the reagents is soluble, and which melt or significantly soften in the proper temperature range, as is well known to those skilled in the arts of the chemical and polymer sciences.

Figure 5:
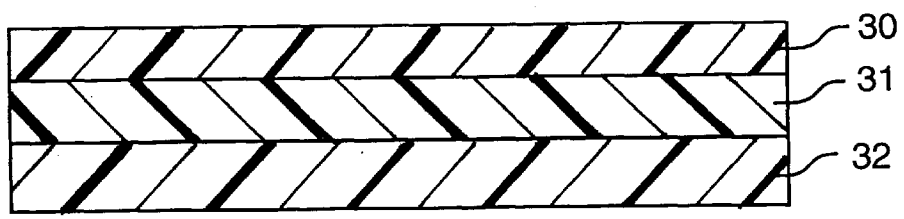
FIG. 5 is a cross-sectional illustration showing a substrate having a matrix coated thereon and associated heating means.

In one embodiment of the invention, the mixture containing the matrix and the reagents is incorporated into a paint or ink that may be deposited on the surface of a heater. It is desirable to formulate a suitable deposition mixture, which does not produce the test gas under ambient conditions. As shown in FIG. 5, the paint or ink coating 30 lies on substrate 31 with underlying heating element 32.

Using carbon monoxide generation as an example, as the complex, bis(iron cyclopentadienyl biscarbonyl), is insoluble in water, an aqueous based ink or paint formulation does not facilitate reaction between the reagents. Formulation of an ink or paint also involves the inclusion of a film forming compound, the so-called "vehicle," to bind the reagents and the matrix and hold them on to the substrate. In addition, rheology modifiers and surfactants may also be added to the ink mixture to improve the rheology of the ink mixture to facilitate application, and to mitigate any adverse effects of the vehicle and other components on the reaction between the reagents in the matrix once the matrix material is melted.

Vehicles used in paint formulations are typically polymeric materials which form adherent and flexible films on the surface to which the paint is applied. For a water based paint, the vehicle may, for example, be a water-soluble polymer such as polyacrylic acid, or a water emulsifiable polymer such as latex emulsions.

The vehicle can be added to the mixture prior to depositing it onto a surface, such that the vehicle holds both the matrix and the reagents to the surface. When it is desirable to generate test gas, heat is applied to the surface, and the matrix melts, thus allowing dissolution of one or more of the reagents within the matrix. The dissolved reagent or reagents can then react with the other reagents to produce the test gas. The vehicle will usually not melt, but instead it will retain the macroscopic three-dimensional structure of the coating. The production of test gas though is facilitated if the vehicle softens with temperature, as this increases the mobility of the matrix and dissolved reagents within the vehicle. The addition of plasticizers to the vehicle not only improves the flexibility of the vehicle at ambient temperature and, therefore, improves the mechanical properties of the coating, but the plasticizers also aid in softening of the vehicle upon heating.

The classification of ingredients as the reagent, matrix or the vehicle is based on chemical and physical functions. Various materials, or combinations of materials may provide one or more of these basic functions. For example, some film forming polymers, such as polyethylene oxides, can be used as both the vehicle and the matrix. Upon heating, the viscosity of the polymer film decreases to the point wherein one or more of the reagents can dissolve into the polymer and have sufficient mobility to reach the other reagent or reagents and thus produce the test gas.

Similarly, plasticizers such as propylene glycol, may also act as a matrix when combined with a suitable vehicle. At low temperature, the vehicle structure and the plasticizer will be fixed in place, though with some innate flexibility, or plasticizer enhanced flexibility. At high temperatures, the mobility of the plasticizer will increase, as the vehicle becomes more flexible, and thus the plasticizer may be able to dissolve on or more of the reagents and allow the movement of the reagent(s) to the other reagent(s) and result in test gas being generated.

There are many functional additives, which are commonly incorporated in inks, paints and other coatings, which may be included in a test gas formulation of the present invention. The use of these additives as well as many alternative components are well known in the art of formulation. See, for example, McCutcheon's, Vol. 2: Functional Materials, Publ. MC Publishing Co., Glen rock N.J., (1992).

Example 1 provides an example of a formulation for a paint or coating that will produce carbon monoxide gas when heat is applied to the dried paint.

| | |
|---|---|
| Polyethylene powder | 1.5 g |
| Manganese dioxide | 2.0 g |
| Bis(iron cyclopentadienyl dicarbonyl) | 0.2 g |
| Carbopol | 0.06 g |
| Aqueous polyurethane emulsion | 3.0 ml |
| Sodium dodecylsulfate | 0.05 g |

All the ingredients are mixed together to produce a viscous ink, which can be printed or otherwise applied onto a heating element. The ink can be dried at ambient temperature, or the drying can be accelerated by gently warming in an oven at about 50° C., for example. Upon activation of the heater (after the ink has dried) to a temperature of approximately 130° C., carbon monoxide test gas will be produced. The printing of the gas-generating element can be performed by conventional means, such as by screen printing. The two reagents employed in Example 1 are manganese dioxide and bis (iron cyclopentadienyl bis carbonyl), the matrix is low density polyethylene powder, and the vehicle is an aqueous polyurethane emulsion. A small amount of Carbopol, a thickening agent, available from BF Goodrich Inc., Cleveland Ohio is added to add viscosity to the mixture, together with a small amount of sodium dodecylsulfate, a surfactant, that is added to improve the mechanical properties of the mixture and the wetting of the substrate.

The formulation in Example 1, is provided for illustration only. There are many ways in which the recipe can be modified, for example by substituting reagents, or the rheology modifier or surfactant, which are well known to those skilled in the art. Typical formulations for a wide variety of inks and other related mixtures which can be used to develop new formulations may also be found in standard texts, such as the 35 volume series, "The Chemical Formulary" from the Chemical Publ. Co., Brooklyn, N.Y.

The selection of other reagents can be made according to the overall medium of the solution. If the matrix material is hydrophobic, the reagents may be selected so that one or more of the reagents is soluble in the molten matrix. Typically, to increase the solubility of an ionic reagent with an anion, such as a sulfide, cyanide, sulfite, then the cation may be a tetralkylammonium ion, such as tetrabutylammonium or tetraethylammonium ion. If the matrix material is polar, then the alkaline metal cations will typically promote solubility. Solubility can also be increased by the addition of complexing agents. For example, the addition of the macrocycle 18 Crown 6 crown ether (1,4,7,10,13,16-hexaoxacyclooctadecane) can greatly increase the solubility of alkali metals salts in low polarity, and hydrophobic solvents.

The solubility of ammonium salts in low polarity solvents increases with the use of low charge, bulky anions, such as hexafluorophosphate, and tetraphenylborate. To increase the solubility of ammonium salts in polar media, such as aqueous solution, the use of smaller anions, such as nitrate or, chloride, for example, is effective.

For laboratory preparations of some of the test gases, a strong acid, such as sulfuric acid could be used. While sulfuric acid can be employed, it is a very hygroscopic liquid, and is very corrosive. Instead, solid organic sulfonic acids, such as p-toluenesulfonic acid (MP=103–106° C.) or 2-naphthalenesulfonic acid (MP=124° C.), both of which are fairly strong acids, are preferred.

This approach to varying the counter ion of acids, bases and salts, and the addition of complexing agents is well known to those skilled in the art.

Other gases can also be generated using this invention, using the same methods as described herein. There are many chemical reactions which are known, and often used to produce gases for laboratory use that can be produced with this invention. Examples of such reactions can be found in many standard chemistry text books, such as Merck Index, Twelfth Edition, 1996, for example. Several examples of these gases and reactions are the following.

For ammonia test gas production, for example, creation from an ammonium salt by action of a strong base such as by the reaction of sodium hydroxide, on ammonium sulfate, may be employed by reaction (1).

$$2NaOH+(NH_4)_2SO_4 \rightarrow Na_2SO_4+2NH_3+2H_2O \quad (1)$$

Reaction (2) involves the production of chlorine by reaction of manganese dioxide with hydrochloric acid, or by reaction of manganese dioxide with a chloride salt in the presence of a strong acid.

$$MnO_2+2MCl+2RSO_3H \rightarrow MnO+Cl_2+2MO_3SR+H_2O \quad (2)$$

Reaction (3) creates hydrogen by reaction of a metal with an acid to produce hydrogen and the metal salt, such as, for example, the reaction of iron powder with a strong acid.

$$Fe+2H^+ \rightarrow Fe^{2+}+H_2 \quad (3)$$

Displacement of cyanide employing reaction (4) which involves the reaction of a strong acid with sodium cyanide.

$$NaCN+H^+ \rightarrow Na^++HCN \quad (4)$$

Displacement of hydrogen sulfide ($H_2S$) may be achieved by reaction (5) by the action of strong acids on metal sulfides.

$$FeS+2H^+ \rightarrow Fe^{2+}+H_2S \quad (5)$$

Reaction of a strong acid with a sulfite salt, such as sodium sulfite, to produce sulfur dioxide is shown in reaction (6).

$$Na_2SO_3+2H^+ \rightarrow 2Na^++SO_2+H_2O \quad (6)$$

There are many other reactions, which can be used to produce desired test gases, which can be incorporated into a gas-generating element using this invention. The examples provided herein are intended for illustration only, and are not intended to limit the scope of this invention.

Figure 6:
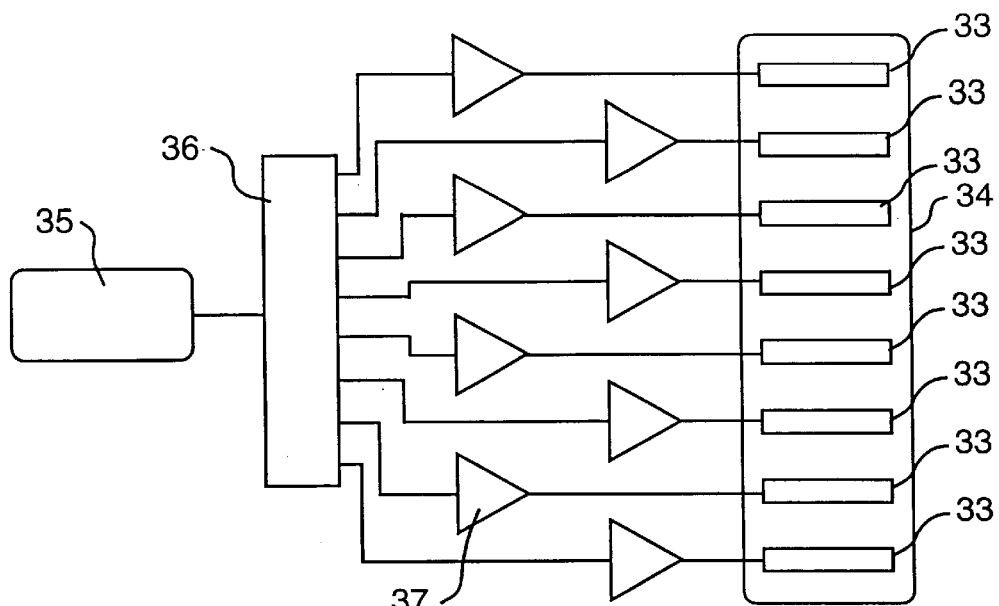
FIG. 6 is a schematic circuit diagram showing a form of electrical system for heating the matrix material to generate test gases in accordance with the present invention.

In one embodiment of this invention, with reference to FIG. 6, a plurality of the test gas-generating elements 33 are produced in an array. The entire array forms a gas-generating unit 34. Every time that test gas is required, a new element 33 can be activated. A representation of a circuit that would perform this task is shown in FIG. 6. The signal to initiate the production of test gas is provided by a microprocessor 35 or other controller, which sends a signal to the multiplexer 36 indicating which gas-generating element 33 is to be activated. A typical signal may, for example, be a change in the potential, from one logical state to another. The multiplexer 36 output for the selected gas-generating element 33 is passed through an amplifier 37, which provides signals with sufficient power to the gas-generating element 33. This applied signal causes the heater (not shown) comprising part of the selected gas-generating element 33 to reach a sufficient temperature for the matrix material to melt or soften to allow the reagents to react chemically and generate the test gas. After the gas has been generated for the required length of time, the microprocessor 35 will change its output signal to the multiplexer 36, to the logical state for no gas production. The multiplexer 36 output to the activated gas-generating element 33 will change it logical state and the amplifier 37 will cease to apply a potential to the gas-generating element 33. The next time gas is required, the microprocessor 35 may either select the same gas-generating element 33 if it still retains sufficient capacity to produce gas, or it may select another gas-generating element within the gas-generating unit 34. The design decision of whether to have the microprocessor 35 use a gas-generating element 33 one time or more than one time will depend on the application and on the particular implementation of this invention. Also, if desired, different gas-generating elements 33 may be created to create different test gases.

Figure 7:
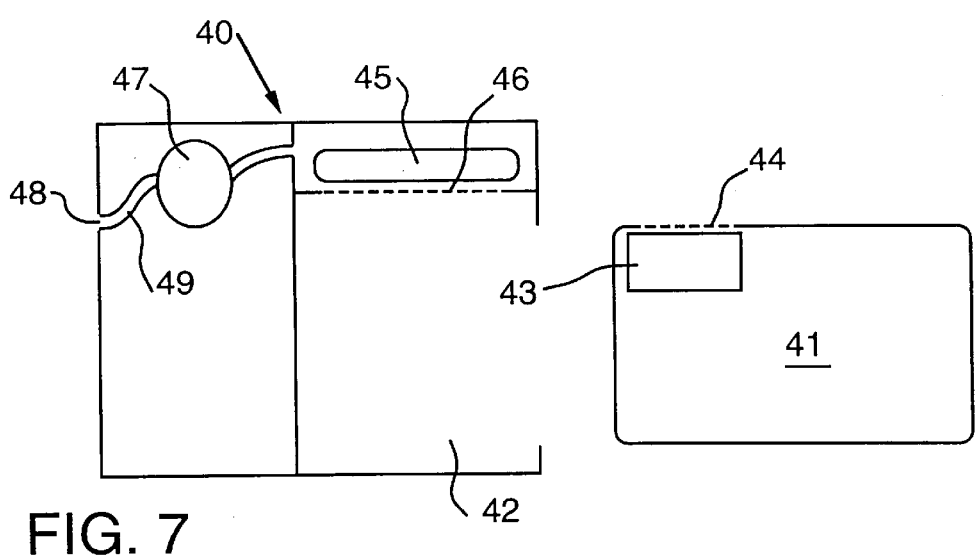
FIG. 7 is a partially schematic elevational view showing a test gas-generating unit and a cooperating gas detection instrument of the present invention.

This invention can be implemented in a number of ways. In one embodiment of the invention, shown in FIG. 7, the gas-generating unit 45 can be incorporated into a calibration device 40 that produces test gas. This calibration device 40 connects with the gas detection instrument 41, by incorporating a cavity 42 into which the gas detection instrument 41 fits. The gas detection instrument 41 contains one or more gas sensors 43, which are exposed to the environment outside of the gas detection instrument by a protective gas porous screen 44. The calibration device 40 is designed such that when the instrument 41 is inserted into cavity 42 of the calibration device 40, the sensor 43 within the gas detection instrument 41 is in close proximity to the gas-generating unit 45 disposed within the calibration device 40. Typically there will be a protective porous grill 46 between the gas detection instrument 41 and the gas-generating unit 45. Activation of the gas-generating elements will result in the flow of test gas through the grill 46 and through the adjacent screen 44 on the gas detection instrument 41, to the gas sensor 43. This flow of test gas from the gas-generating unit 45 to the sensor may be by natural gas diffusion, or alternatively, the calibration device 40 may contain a pump 47 which draws ambient air into the calibration device through opening 48 and through an optional filter (not shown) to remove contaminants. The pump 47 causes a flow of air through tubing 49 adjacent to the gas-generating unit 45. The delivered air flow mixes with the gas generated by the gas-generating unit 45. The resulting mixture flows through the grill 46, and over the porous screen 44 protecting the sensors 43 in the gas detection instrument 41.

Figure 8:
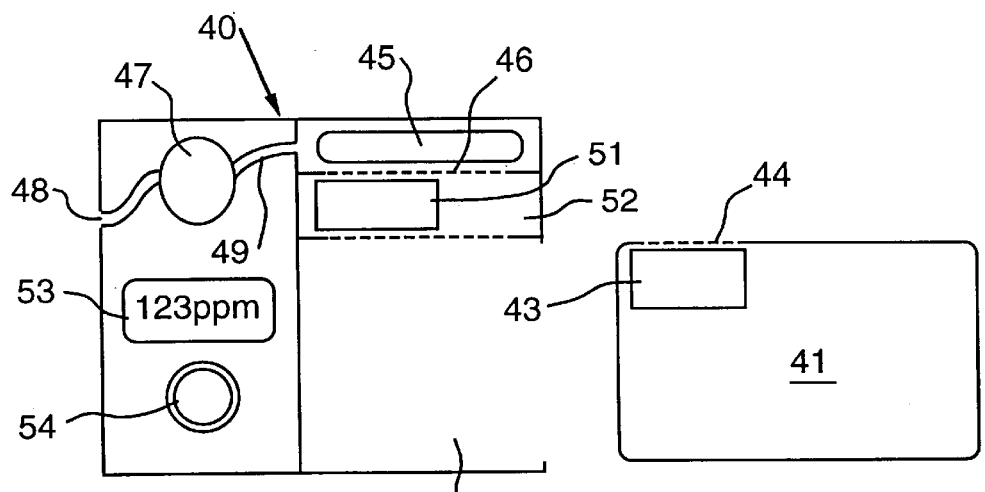
FIG. 8 is a schematic illustration of a modified form of the system of FIG. 7.

In a further embodiment of this invention, shown in FIG. 8, the calibration device 40 can contain an additional gas sensor 51, which is sensitive to the gas to be generated. This sensor is located within gas flow path 52, between the gas-generating unit 45 and the cavity 42 wherein the gas detection instrument 41 is inserted. The gas sensor 51 is connected to conventional electronics (not shown), similar to that used in the present art for gas detection instruments. The art of construction of gas sensors and detection instruments is well known in the prior art, as illustrated by the following citations (S. C. Chang, J. R. Stetter, C. S. Cha, *Talanta*, (1993), 40, 461; C. F. Cullis, J. G. Firth, (Eds.) "Detection and Measurement of hazardous Gases", Heinemann, London, 1981; P. T. Moseley, J. Norris, D. E. Williams, "Techniques and mechanisms in gas Sensing" Adam Hilger, Bristol, 1991; J. C. Fidler, J. P. Bobis, W. R. Penrose, J. R. Stetter, U.S. Pat. No. 5,198,771; J. M. Fruhwald, in U.S. Pat. No. 4,642,172; and G. J. Jones, H. A. Buckenham, B. S. Hobbs, P. Gotley, in U.S. Pat. No. 4,776,203). Gas sensor 51 serves to provide a measure of the gas concentration produced by the gas-generating unit 45, after dilution with the air flow from pump 47. By calibrating the sensor 51 with a gas of known concentration, the reading on the display 53 will indicate the concentration of the gas produced by the calibration device 40. If the concentration of gas coming out of the calibration device 40 is known, then the calibration device 40 can be used to calibrate gas detection instruments 41. Subsequently, the calibration device 40 can be used as a source of calibration gas for the calibration of gas detection instruments or other devices requiring a known concentration of test gas. If the output from the gas-generating unit 45 does change with time, especially if the same gas-generating element 33 is used for a long duration, the concentration shown in the display 53 will decrease and the user can then adjust the calibration of the gas detection instrument 41 accordingly.

In a further embodiment of this invention, the gas-generating elements 33 within the gas-generating unit 34 are designed such that changing the magnitude of the potential applied to the gas-generating element 33, can vary the concentration of the gas generated. A method for achieving this capability is described herein. As shown in FIG. 8, the output gas concentration from the calibration device 40 can be set at a predetermined value by the user, by use of dial 54. The calibration device will vary the potential applied to the gas-generating element 33, so as to maintain the output gas concentration to the said predetermined value, until the reagents on the gas-generating element 33 are completely consumed. Once all of the reagents have been consumed, then another gas-generating element 33 is selected, either manually or by the microprocessor or other controller of the calibration device 40. Once all of the gas-generating elements 33 have been consumed, then the gas-generating unit 34 needs to be replaced.

Figure 9:
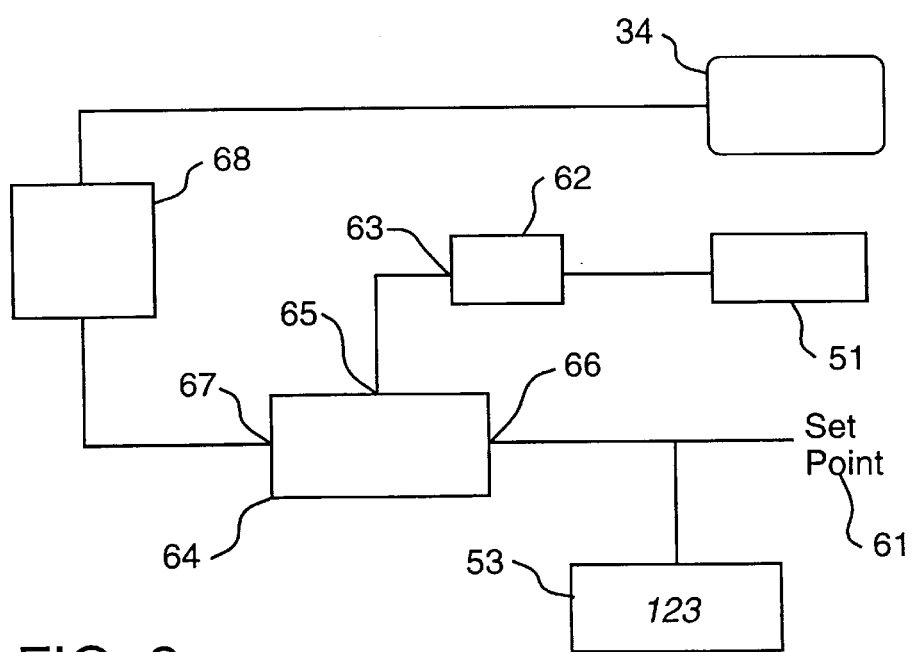
FIG. 9 is a schematic diagram of a circuit for use in generating a known test gas concentration.

A representation of the circuit is shown in FIG. 9. The user selects a set-point with dial 54 (FIG. 8), which determines the value of the set-point 61. This set-point may be displayed as a reading in units of gas concentration (e.g. parts per million) on the display 53, as an aide to the user. Power is applied to the gas-generating unit 34, and the gas produced reaches the gas sensor 51. The sensor circuit 62 drives the sensor 51, and provides a signal at its output 63, which is connected to a comparator 64. The signal from the sensor 51 which is introduced at the comparator input 65 is compared with the signal from the setpoint 61 which is introduced at the other input 66 of comparator 64. If the signal at the comparator input 65 corresponding to the gas concentration is greater than the signal at the input 66, then the output 67 from the comparator 64 will be set to a logical state to stop production of the gas by the gas-generating unit 34. If the signal at the comparator input 65 corresponding to the gas concentration is less than the signal at the input 66, then the output 67 from the comparator 64 will be set to a logical state to increase production of the gas by the gas-generating unit 34. The output 67 from the comparator 64 is connected to the gas-generating element control circuit 68. The gas-generating control circuit 68 takes the logical signal from the output 67 of the comparator 64 and provides a suitable waveform, selection of individual elements 33, (if the gas-generating unit 34 comprises an array of gas-generating elements 33 is being used), and amplification to drive the gas-generating unit 34. Variations in the specific circuits disclosed herein may be, if desired, found in standard texts. See for example, P. Horowitz, W. Hill, "The Art of Electronics", $2^{nd}$ Edition, Cambridge University Press, 1989.

Figure 10:
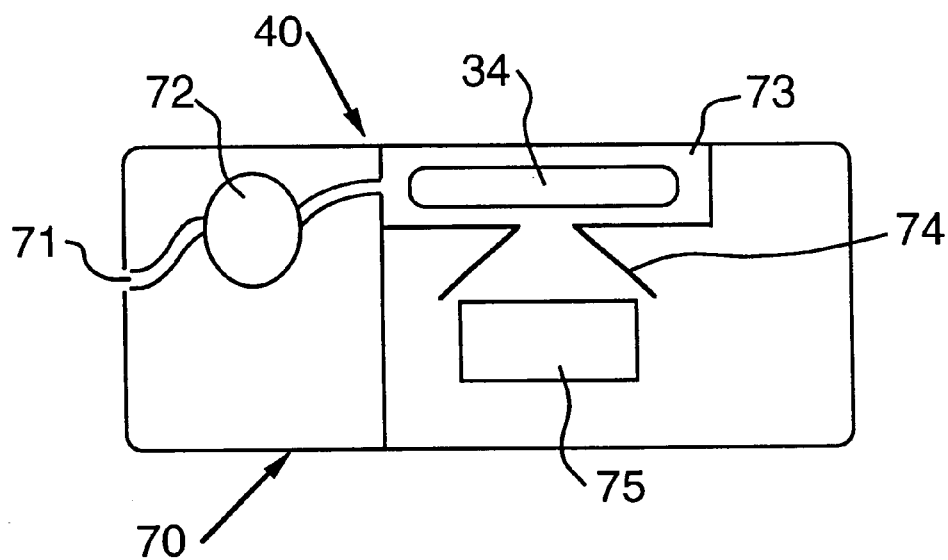
FIG. 10 is an illustration of a gas detection instrument incorporating a gas-generating unit for in situ testing.

In another embodiment of this invention, the gas-generating element is incorporated into a gas detection instrument 70, as shown in FIG. 10. Only the gas flow path of the gas detection instrument is shown, the rest of the instrument, housing, electronics battery, display may be conventional. During normal operation of the gas detection instrument 70, ambient air is drawn in through portal 71 by the pump 72. This air is passed through the chamber 73 containing the gas-generating unit 34. The gas-generation unit 34 is not activated during the normal use of the instrument 70. The air passes from the chamber containing the gas-generating unit to a manifold 74 which feeds the gas to the gas sensor 75. During normal operation of the gas detection instrument 70, the output of the sensor 75 is determined by the composition of the ambient air drawn into the instrument 70 by the pump 72. During a gas test of the gas detection instrument 70, the pump 72 draws air in through portal 71 and this air passes into the chamber 73 containing the gas-generating unit 34. During the gas test, the gas-generating unit 34 is activated and the gas-generating unit 34 produces a gas, which mixes with the air flowing in the chamber 73 to produce the test gas mixture. This gas mixture then passes through the manifold 74 to the gas sensor 75. The output from the sensor 75 is monitored for a given length of time, and the output signal from the sensor 75 monitored. Depending on the output signal and the performance specifications of the gas detection instrument 70, the sensor 75 may be deemed satisfactory, the calibration parameters may be adjusted, or the sensor 75 may be deemed unsatisfactory and in need of replacement. At the completion of the gas test, the gas-generating unit 34 is deactivated, and the gas detection instrument 70 will again provide monitoring of the ambient atmosphere.

The range of gas to air mixture will depend on the gas type and the instrument. Typically, the gas flow rate used to calibrate a sensor commonly used for safety applications is in the range of 0.2 to 2 liters per min. with 0.5 to 1 l/min being commonly used. A preferred concentration range to calibrate a sensor is near the alarm threshold limits, which for safety gas monitors are usually based on the permissible exposure limits (PELs). The OSHA PELs vary greatly from gas to gas. For example, for carbon monoxide the eight hour TWA PEL is 50 ppm, sulfur dioxide is 5 ppm and chlorine dioxide is 0.1 ppm. (NIOSH Pocket Guide to Chemical Hazards, Publ. U.S. Department of Health and Human Services, June 1997) The flow rate chosen then will depend on the rate of production of the gas from the gas-generating element, the pump speed which controls the gas flow rate and the desired concentration. The relationship between these parameters can be written mathematically as:

Concentration of gas=Rate of production of gas from generator/ gas flow rate

The range of air to gas mixtures will vary with the gas type and application. Employing carbon monoxide as an example, the typical concentrations to calibrate a carbon monoxide sensor vary from 25 to 500 ppm, with a gas flow rate varying from 0.20 to 2 liters per minute. The rate of carbon monoxide generation corresponding to 25 ppm at 0.2 l/min is $2 \times 10^{-7}$ moles/s, or ~6 µg/s carbon monoxide. The rate of carbon monoxide generation corresponding to 500 ppm at 2 l/min is $4 \times 10^{-5}$ moles/s, or ~1 mg/s carbon monoxide.

The gas test may be initiated at the instigation of the user, to allow the user to determine whether the gas detection instrument 70 is operating correctly. In another embodiment of the invention, the activation of the gas-generating unit 34 can be under the automatic control of a microprocessor or other controller within the instrument (not shown), allowing the instrument 70 to test the function of gas detection instrument without the need for human intervention. The gas detection instrument may also be microprocessor controlled. Suitable enhancement, storage and output from the microprocessor may be provided, as desired.

In a further embodiment of this invention, it has been found that the rate of test gas production and the amount of gas produced both increase with temperature. It is also known that the temperature of an electrical resistance heater can be increased by increasing the electrical power delivered to the heater, by increasing either the current (I) passing through the electrical resistance (R) or the potential (E) applied to the electrical resistance, based on the well known equation:

Power=$I^2R=E^2/R$

Increasing the electrical power delivered to the heater can increase the output from a gas-generating unit.

The ability to control the temperature and as a result the amount of gas produced can be enhanced if the resistance per unit length of a linear resistive heater element is not constant. This configuration causes the steady state temperature to vary with distance along the heater after a potential is applied to the heater. As the potential is increased, a greater surface area of the heater will reach a temperature sufficient for the production of the test gas.

To illustrate this embodiment, consider a resistive heating element comprised of four resistors in series, with resistances $R_1$, $R_2$, $R_3$ and $R_4$, respectively. Assume that the resistance of each resistor decreases along the chain, such that the resistance values are in the order $R_1 > R_2 > R_3 > R_4$. Also assume that these resistors are each coated with the gas-generating reagent and matrix mixture. When a potential is applied across the four resistors, between $R_1$ and $R_4$, a current (i) will flow through the four resistors, and the power at each resistor is respectively:

$$i^2R_1 > i^2R_2 > i^2R_3 > i^2R_4$$

Therefore provided the thermal mass, thermal conductivity and emissivity of the four resistors and their environs are similar, then the relative temperature (T) of the four resistors will be respectively:

$$T_1 > T_2 > T_3 > T_4.$$

At low potential, test gas would be produced from coated resistor $R_1$, but not from the other coated resistors, and as the potential was increased, test gas would be produced from successive resistors, until all four resistors were at a sufficient temperature to release test gas from the gas-generating mixture.

Figure 11:
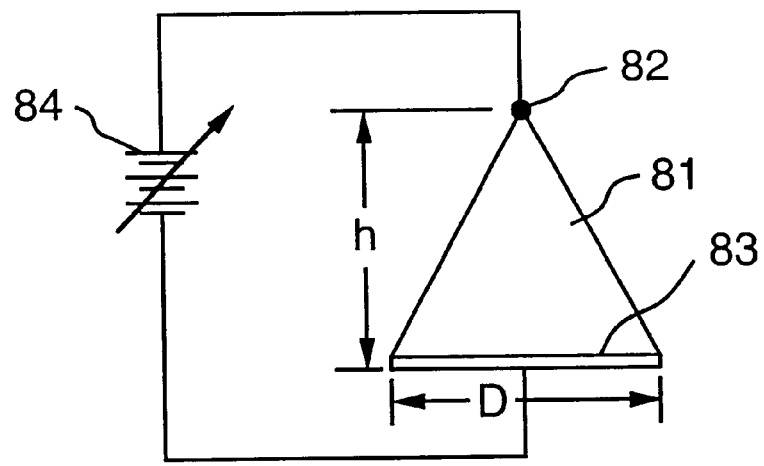
FIG. 11 is a schematic diagram showing a heat generating means having modified temperature controls.

In another example, consider a gas-generating element composed of a printed film resistive heater 81 of constant bulk resistivity (p) and thickness (t), but of varying width (d), such that the resistive heater 81 formed an isosceles triangle shape, as is shown in FIG. 11. Assume that the potential from power supply 84, is applied between the tip of the triangle 82 and the lower flat edge 83, so that the resistance per unit length increases along the vertical axis of the triangle. By consideration of the geometry of the heater 81, it can be easily shown that the electrical power per unit area (dP/dA) of the heater 81 is given by the following equation:

$$dP/dA = i^2 \, {}^{i\rho h^2}/D^2tL^2$$

where P is power, A is area, ρ is bulk resistivity, h is the length between the tip of triangle 82 and the lower flat edge 83, D is the length of the lower flat edge 83, t is the thickness, and L is the length up the triangle heater 81 from the tip 82 to the flat edge 83. L varies from zero at the tip of the triangle 82 to L equals h at the lower flat edge 83. From this relationship, it is clear that since $L^2$ is in the denominator, that the power (heat produced) per unit area of the heater 81 varies as the square of the distance along the axis from the lower flat edge 83 to the tip 82. If a potential is applied between the tip 82 and the lower flat edge 83 of the triangle heater 81, then this square relationship of L will give a very large temperature profile along the length of the heater 81. From this discussion, it has been shown that the geometry of the heating element 81 can also be used to control the temperature of the heating element 81. Controlling the temperature allows the amount of test gas generated to be controlled, by controlling the electrical power supplied to the heater. The triangular shape and thermal analysis of the heater 81 is provided to illustrate that the geometry can be used to control the temperature. Other geometric shapes can be used, if desired.

It will be appreciated that the various embodiments of the present invention are adapted to provide rapid generation of test gases such that the gas detection instruments will respond with an appropriate alarm when the test gas exceeds a predetermined concentration in well under a minute and preferably within about 20 to 30 seconds after initiation of generation of the test gas.

The present invention, therefore, provides an efficient means of employing a thermally activated chemical reaction which facilitates reagents interacting to produce a desired test gas in order to test or calibrate gas detection instruments. All of this is accomplished while permitting use with conventional gas detection instruments having the test gas generated externally of the gas detection instruments or, in the alternative, providing the test gas generator apparatus in such a way that it is either disposed within the gas detection instruments or can receive portions of the gas detection instruments.

Whereas particular embodiments have been described herein for purposes of illustration it will be evident to those skilled in the art that numerous variations of the details may be made without departing from the invention as defined in the appended claims.

What is claimed is:

1. A method of testing gas detection instruments comprising
   providing at least two reagents and a matrix material,
   immobilizing at least two said reagents on said matrix material,
   subsequently heating said matrix material until said matrix material permits movement of said reagents,
   generating a gas responsive to a chemical reaction between said reagents, and
   employing said gas to test said gas detecting instrument.

2. The method of claim 1 wherein
   said heating of said matrix material occurs until said matrix material softens to permit movement of said reagents.

3. The method of claim 1 including
   effecting said heating of said matrix material until it melts.

4. The method of claim 1 including
   effecting said heating of said matrix material to about 60 to 400° C.

5. The method of claim 1 including
   employing a first matrix material to immobilize a first said reagent, and
   employing a second matrix material to immobilize a second said reagent.

6. The method of claim 1 including
   immobilizing a first said reagent in a first portion of said matrix material, and
   immobilizing a second said reagent in a second said portion of said matrix material.

7. A method of testing gas detection instruments comprising
   providing at least two reagents,
   immobilizing at least two said reagents on said matrix material,
   immobilizing a first said reagent in a first portion of said matrix material,
   immobilizing a second said reagent in a second said portion of said matrix material;
   inserting a third portion of said matrix material between said first matrix portion and said second matrix portion to separate said first and second reagents;
   introducing at least one of said reagents into a matrix material,
   subsequently heating said matrix material until said matrix material permits movement of said reagents,
   generating a gas responsive to a chemical reaction between said reagents, and
   employing said gas to test said gas detecting instrument.

8. The method of claim 1 including
   effecting said heating to a temperature of about 90 to 150° C.

9. The method of claim 1 including
   employing said method to generate a gas selected from the group consisting of carbon monoxide, ammonia, chlorine, hydrogen, hydrogen cyanide, hydrogen sulfide and sulfur dioxide.

10. The method of claim 2 including
    employing electrically energized means to effect said heating.

11. The method of claim 1 including
    employing as said at least one said reagent a reagent selected from the group consisting of a transition metal sulfide, an alkali metal sulfide, and an alkaline earth metal sulfide.

12. A method of testing gas detection instruments comprising
    providing at least two reagents,
    introducing at least one of said reagents into a matrix material,
    subsequently heating said matrix material until said matrix material permits movement of said reagents,
    generating a gas responsive to a chemical reaction between said reagents,
    diluting said gas; and
    employing said gas to test said gas detecting instrument.

13. The method of claim 1 including
    applying said reagent containing matrix to a substrate as a coating.

14. The method of claim 1 including
    employing as said reagent at least one oxidizing agent selected from the group consisting of manganese dioxide, cerium (IV) salts, permanganate iodate chromate, chlorate and dichromate salts of alkaline metals, alkaline earth metals and tetralkyl ammonium ion.

15. The method of claim 1 including
    controlling the rate of gas generation by controlling the rate of heating.

16. The method of claim 1 including
    employing Bis(iron cyclopentadienyl dicarbonyl) as one said reagent, and
    producing carbon monoxide as said test gas.

17. The method of claim 16 including
    producing said carbon monoxide by oxidizing said Bis (iron cyclopentadienyl dicarbonyl).

18. The method of claim 10 including
    employing a plurality of electrical resistors in effecting said heating, and
    varying the rate of generation of said gas as a function of which said resistors are energized.

19. The method of claim 10 including
    providing an electrical resistor having a thermal output which varies as a function of the amount of said resistor which is energized, and
    energizing at least a portion of said resistor to generate said gas.

20. The method of claim 1 including
    employing a plurality of gas-generating said elements which are reagent containing matrix material, and
    selectively heating said gas-generating elements to generate gas.

21. The method of claim 20 including
    employing microprocessor means to effect said selective heating.

* * * * *

UNITED STATES PATENT AND TRADEMARK OFFICE
CERTIFICATE OF CORRECTION

PATENT NO. : 6,632,674 B1
DATED : October 14, 2003
INVENTOR(S) : P. Richard Warburton It is certified that error appears in the above-identified patent and that said Letters Patent is hereby corrected as shown below:

Column 10,
Line 40, insert -- Example 1 --.

Column 16,
Line 32, equation should read -- $dP/dA = i^2 ph^2/D^2 tL^2$ --.

Signed and Sealed this

Third Day of February, 2004

JON W. DUDAS
*Acting Director of the United States Patent and Trademark Office*